(12) United States Patent
Pellerin et al.

(10) Patent No.: US 10,543,126 B2
(45) Date of Patent: Jan. 28, 2020

(54) EARPLUG DISPENSER

(71) Applicant: Radians, Inc., Memphis, TN (US)

(72) Inventors: Dennis C. Pellerin, Cordova, TN (US); Shannon R. Owens, Horn Lake, MS (US)

(73) Assignee: Radians, Inc., Memphis, TN (US)

( * ) Notice: Subject to any disclaimer, the term of this patent is extended or adjusted under 35 U.S.C. 154(b) by 0 days.

(21) Appl. No.: 15/719,803

(22) Filed: Sep. 29, 2017

(65) Prior Publication Data

US 2018/0021175 A1    Jan. 25, 2018

Related U.S. Application Data

(63) Continuation of application No. 14/863,934, filed on Sep. 24, 2015, now Pat. No. 9,775,746.

(51) Int. Cl.
*A61F 11/08* (2006.01)
*G07F 11/44* (2006.01)
*G07F 11/56* (2006.01)
*G07F 11/54* (2006.01)

(52) U.S. Cl.
CPC ............. *A61F 11/08* (2013.01); *G07F 11/44* (2013.01); *G07F 11/54* (2013.01); *G07F 11/56* (2013.01)

(58) Field of Classification Search
CPC .......... G07F 11/54; G07F 11/56; G07F 11/44; A65F 11/08; B65D 83/0083
USPC ........................................................ 221/265
See application file for complete search history.

(56) References Cited

U.S. PATENT DOCUMENTS

| | | | | |
|---|---|---|---|---|
| 2,176,232 A | * | 10/1939 | Warren | A47F 1/10 221/265 |
| 2,211,452 A | * | 8/1940 | Bowman | A47F 1/035 222/429 |
| 2,227,167 A | * | 12/1940 | Warren | B65D 83/0409 221/265 |
| 3,246,806 A | * | 4/1966 | McBride, Jr. | A01C 9/08 222/203 |
| 3,330,442 A | * | 7/1967 | O'Connor | A47G 19/34 221/265 |
| 3,885,703 A | * | 5/1975 | Neavin | B65D 83/0409 221/202 |
| 4,109,825 A | * | 8/1978 | Weitzman | G07F 11/54 221/122 |
| 5,097,985 A | * | 3/1992 | Jones | A63B 47/002 124/48 |
| 5,219,095 A | * | 6/1993 | Shimizu | G07F 17/0092 221/264 |

(Continued)

FOREIGN PATENT DOCUMENTS

EP    1035035 A1 * 9/2000    ......... B65D 83/0409

*Primary Examiner* — Rakesh Kumar
(74) *Attorney, Agent, or Firm* — Barnes & Thornburg LLP

(57) ABSTRACT

An earplug dispenser is provided which dispenses earplugs directly into a user's hand upon turning of a knob in either a clockwise or counterclockwise direction. The earplug dispenser is designed for quick and efficient replacement of an empty container with a container full of earplugs. The internal delivery components are particularly designed to prevent earplug jamming or sticking and aid in the quick delivery of a desired number of earplugs directly into the user's hand. The design also allows the earplugs to be delivered without relying on a separate opening or port apart from the impeller thereby eliminating the need to use two hands to deliver or dispense the desired earplugs.

14 Claims, 8 Drawing Sheets

(56) References Cited

U.S. PATENT DOCUMENTS

| | | | | |
|---|---|---|---|---|
| 5,259,532 A * | 11/1993 | Schwarzli | ............... | G07F 11/44 221/203 |
| D413,465 S | 9/1999 | Scholey | | |
| 5,954,229 A * | 9/1999 | Scholey | ................. | G07F 11/44 221/186 |
| 6,241,120 B1 | 6/2001 | Scholey | | |
| 6,299,019 B1 * | 10/2001 | Leight | ................... | A61F 15/001 221/186 |
| 6,604,653 B2 * | 8/2003 | Millar | .................... | G07F 11/44 221/203 |
| D524,037 S | 7/2006 | Van Horn | | |
| 7,556,176 B2 * | 7/2009 | Yao | ....................... | G07F 11/007 221/155 |
| 7,743,942 B1 * | 6/2010 | Chang | .................... | G07F 11/44 194/232 |
| 9,045,272 B2 * | 6/2015 | Kim | ....................... | B65D 83/04 |
| 2004/0099295 A1 * | 5/2004 | You | ........................ | A45B 11/00 135/16 |
| 2005/0279760 A1 * | 12/2005 | Yao | ........................ | G07F 11/24 221/265 |
| 2006/0124659 A1 * | 6/2006 | Mosconi | ............. | A47J 31/3623 221/161 |
| 2015/0179018 A1 * | 6/2015 | Rudek | ................... | A61F 15/001 221/186 |
| 2016/0096675 A1 * | 4/2016 | Dai | ...................... | B65D 83/0083 221/277 |
| 2018/0021175 A1 * | 1/2018 | Pellerin | ................. | G07F 11/44 221/265 |

\* cited by examiner

EARPLUG DISPENSER

CROSS-REFERENCE TO RELATED APPLICATION

This application is a continuation of U.S. application Ser. No. 14/863,934, filed Sep. 24, 2015, the contents of which is incorporated herein in its entirety.

BACKGROUND OF THE INVENTION

Earplugs are worn by industrial workers to protect their hearing while working in various noisy environments. As a worker enters a noisy workplace environment, the worker is required to insert earplugs prior to returning to daily work activities. While some workers may choose to reuse earplugs, many workers choose to change out their earplugs throughout the day such as upon arrival or upon returning from a break (e.g., lunch). In such cases, the workers will need to quickly obtain new earplugs from a dispenser strategically located in the workplace.

Various earplugs dispensers are available for implementation in the workplace. Such dispensers are often mounted to a wall near an entrance such that a worker may obtain earplugs upon arrival. Existing earplug dispensers, however, suffer from various shortcomings such as the inclusion of internal components that only move in a single direction, dispensing too few or too many earplugs upon use (earplugs sticking together), hanging up or jamming earplugs inside internal moving parts, or failing to dispense any earplugs at all. Thus, there remains a need in the art for an earplug dispenser that quickly, efficiently dispenses the desired number of earplugs while overcoming the aforementioned shortcomings.

SUMMARY OF THE INVENTION

An earplug dispenser is provided. According to one aspect, the dispenser includes a container for storing earplugs until delivered to the user, a funnel having a top opening and a lower opening, a receiver unit including a band and a barrier having a surface defining a plurality of passages and a central opening, and a rotatable impeller adapted to engage the central opening of the barrier. The impeller includes a top plate having a top surface defining a single aperture adapted to receive one or more earplugs. The impeller also includes a plurality of paddles extending from a bottom surface of the top plate. The impeller further includes a hollow shaft extending downward from the bottom surface of the top plate. According to one embodiment, the hollow shaft further includes a side surface defining a shaft recess for receiving one or more earplugs. According to such an embodiment, the hollow shaft further includes a chute in direct communication with the shaft recess for delivering one or more earplugs from the recess to a user. According to one embodiment, the shaft recess is 180 degrees opposite the impeller aperture.

According to one embodiment, a substantial portion of the top surface of the top plate is angled for directing earplugs to the impeller aperture. According to one embodiment, the top surface angle is between 5 and 45 degrees. According to one embodiment, the top surface includes a fin extending upward for agitating earplugs to facilitate movement toward the impeller aperture. According to one embodiment, the hollow shaft includes a knob portion that includes a plurality of ribs for gripping and rotating by the user. According to one embodiment, the impeller includes two paddles for sweeping at least one earplug into a barrier passage. According to one embodiment, the impeller is adapted to move in both a clockwise and counterclockwise manner. According to one embodiment, the knob portion is adapted to move in both a clockwise and counterclockwise manner. According to one embodiment, the impeller includes a flexible clip adapted to engage a central opening of the barrier. According to one embodiment, the funnel includes a plurality of fingers adapted to engage a surface defining a plurality of holes within a plurality of braces located on the receiver unit.

According to one embodiment, a mount is secured to an exterior surface of the funnel. According to one embodiment, the mount includes at least two flanges adapted to engage a bracket. According to one embodiment, the bracket, mount, or both the bracket and mount are manufactured from an opaque, shaded, colored, translucent, or transparent material. According to one embodiment, the bracket includes a surface defining a plurality of openings adapted to receive an attachment means.

According to one embodiment, one or more of the container, impeller, barrier, or funnel are fabricated from an opaque, shaded, colored, translucent, or transparent material. According to one embodiment, the container is fabricated from paper. According to one embodiment, the container is fabricated from cardboard or fiberboard. According to one embodiment, the container is fabricated from corrugated cardboard or corrugated fiberboard. According to one embodiment, the container is fabricated from a paper bag. According to one embodiment, the container is fabricated from a plastic or a plastic bag.

According to another aspect, a method of dispensing earplugs is provided. The method includes the steps of providing a dispenser for delivering earplugs as provided herein and turning the rotatable impeller either clockwise or counterclockwise to dispense at least one earplug into the user's hand. The container includes at least one earplug for dispensing to the user.

According to another aspect, an earplug dispenser kit is provided. The kit includes a dispenser as provided herein and set of instructions for use. The set of instructions may be located on an exterior surface of the container or may be provided separately. The dispenser optionally includes a mount located on an exterior surface of the funnel and a bracket. The container optionally includes one or more earplugs.

DETAILED DESCRIPTION OF THE INVENTION

An earplug dispenser is provided which dispenses earplugs directly into a user's hand upon turning of a knob in either a clockwise or counterclockwise direction. The earplug dispenser allows for quick and efficient replacement of an empty container with a container full of earplugs. No disassembly of any delivery component is required when the container becomes empty and new earplugs are required. The container may be of any standard size or shape as well as disposable or recyclable. The internal delivery components are particularly designed to prevent jamming or sticking and aid in the quick delivery of a desired number of earplugs directly into the user's hand (or palm). The design also allows the earplugs to be delivered without relying on a separate opening or port apart from the impeller chute thereby eliminating the need to use two hands to deliver or dispense the desired earplugs.

The earplug dispenser as provided herein is particularly suited to dispense foam earplugs (e.g., open-cell polymeric foam). Such foam earplugs are adapted to and capable of being compressed, expanded and ultimately fitted within a user's ear canal. The earplugs may be formed in various colors, including high visibility colors, according to the end user's preference or industry-specific guidelines.

Figure 1:
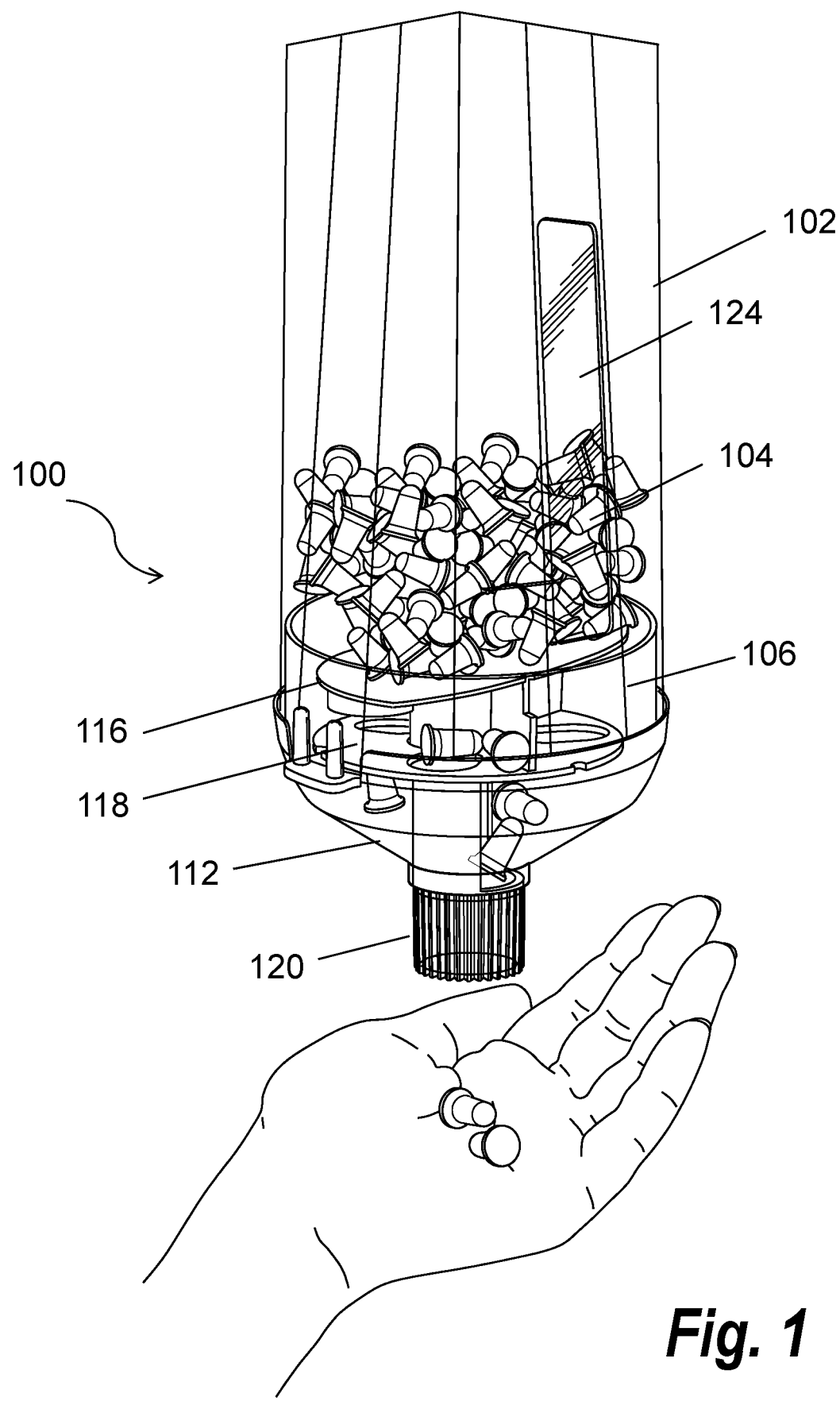
FIG. 1 is a perspective view of an earplug dispenser according to one embodiment.

As shown in the embodiment of FIG. 1, an earplug dispenser 100 includes a container 102 that stores a plurality of earplugs 104 until delivery to the end user. The container 102 includes a translucent or transparent window 124 thereby allowing a user to assess the need to replace an empty container 102. Although not illustrated, the container 102 may include a cap that is easily removed to allow the container 102 to be filled with earplugs 104. The container 102 includes a mouth or opening 106 that engages a band 141 of a receiver unit 143 (see also FIG. 5). The container 102 and band 141 may engage one another according to any known attachment mechanism that allows easy removal and replacement of the container 102. According to one embodiment, the mouth 106 of the container 102 is placed over an exterior surface 170 of the band 141 of the receiver unit 143 (see also FIG. 5). Thus, the mouth 106 of the container 102 is of a size that allows for a tight fit around the exterior surface 170 of the band 141. The funnel 108 includes a tapered portion 112 and lower opening 114 (see also FIGS. 3A and 3B). The funnel 108 is constructed to accommodate a rotatable impeller 116. As described herein in further detail, the rotatable impeller 116 and barrier 118 work together to deliver the desired number of earplugs 104 through the impeller 116 upon rotation (clockwise or counterclockwise) of a knob portion 120 on the impeller 116 by a user.

Figure 2A:
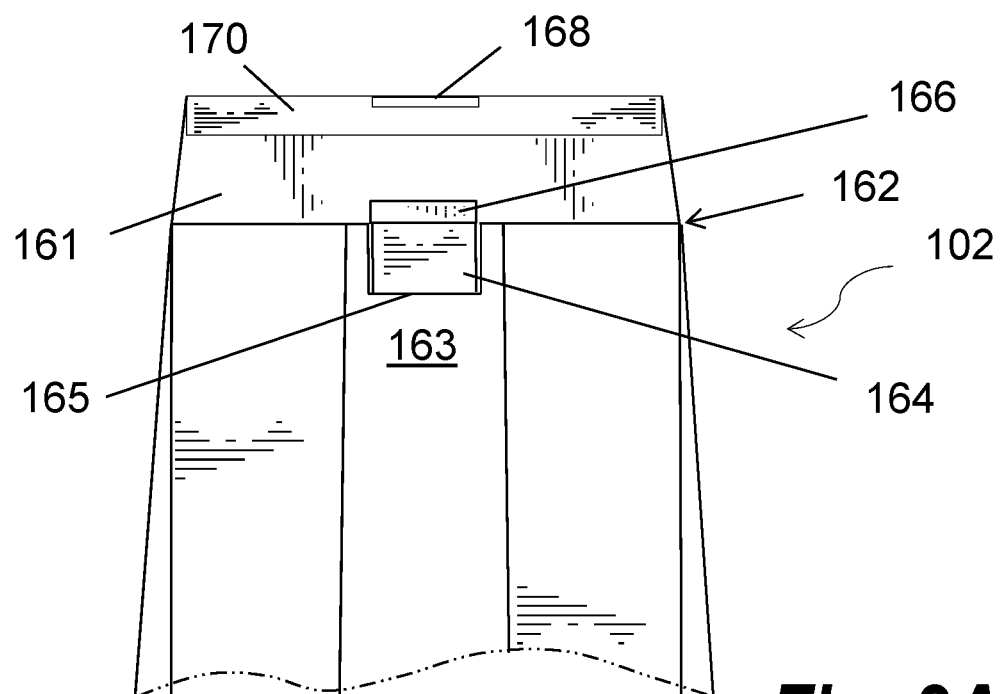
FIG. 2A is a front view of a container of an earplug dispenser according to one embodiment with the top slightly open.
Figure 2B:
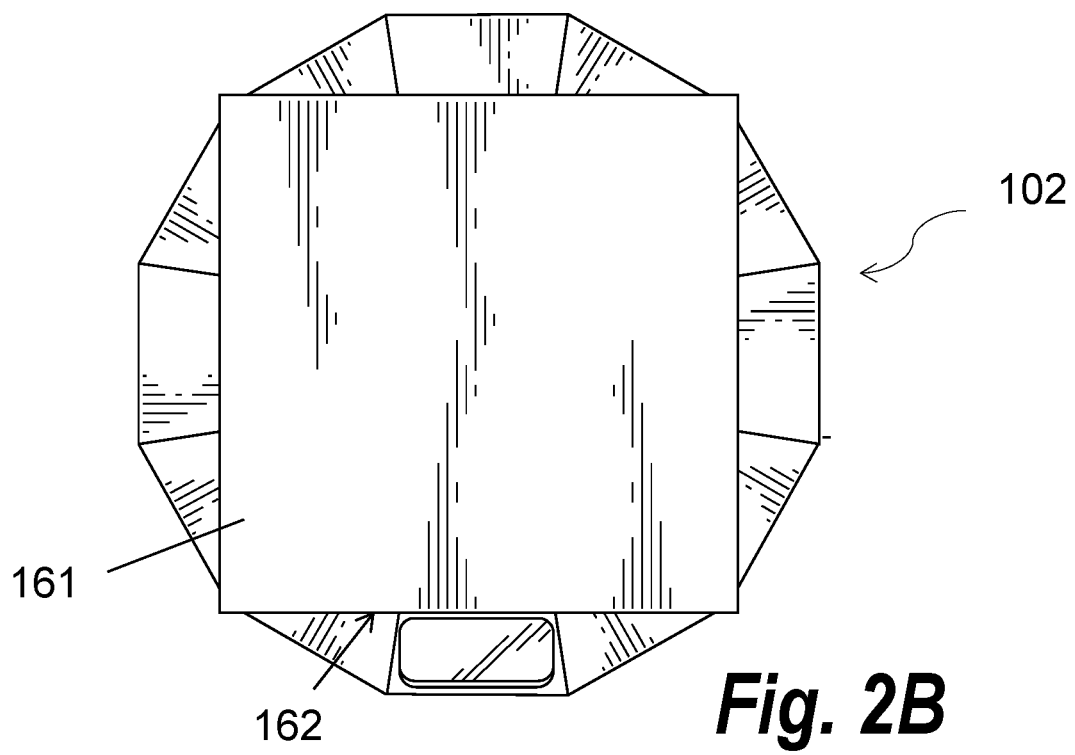
FIG. 2B is a top view of a container of an earplug dispenser according to one embodiment with the top closed.

As illustrated in FIGS. 2A and 2B, the container 102 includes a foldable top 161. The foldable top 161 is shown in an open position in FIG. 2a and in a closed position in FIG. 2B. The top 161 includes a hinged portion 162 allowing the top 161 to move or fold from a closed position to an open position, and vice versa, for depositing within or retrieving earplugs (not shown) from the container 102. An exterior surface 163 of the container 102 includes a flexible flap 164. Although not illustrated, a set of instructions for use may be located on an exterior surface 163 of the container 102. The flexible flap 164 includes a hinged portion 165 allowing the flap 164 to move outward and inward relative to the exterior surface 163 of the container 102. The flap 164 includes at least one tooth 166. The tooth 166 is adapted to engage or enter and be secured within a complimentary cavity 168 located on a curb portion 170 of the top 161. When the tooth 166 in engaged in the cavity 168, the top 161 is secured in a closed position. To open the top 161, the flap 164 is pulled outward thereby pulling the tooth 166 out of the cavity 168. The top 161 may then be pivoted along the hinge portion 162 upward to allow a user access to the container 102.

Figure 3A:
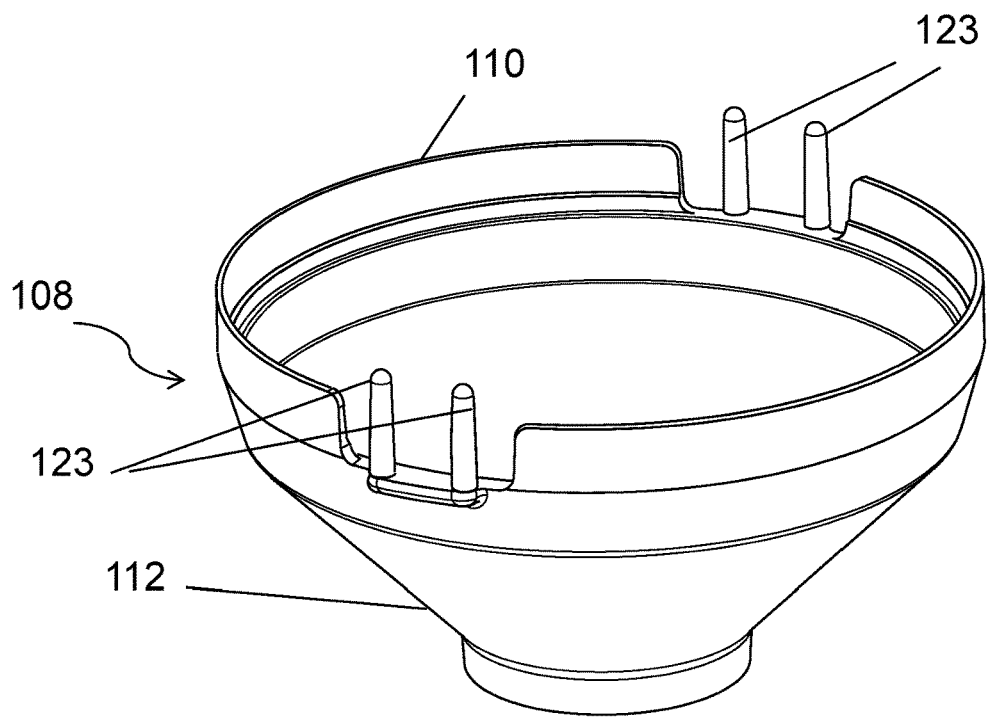
FIG. 3A is a perspective view of a funnel of the earplug dispenser of FIG. 1.
Figure 3B:
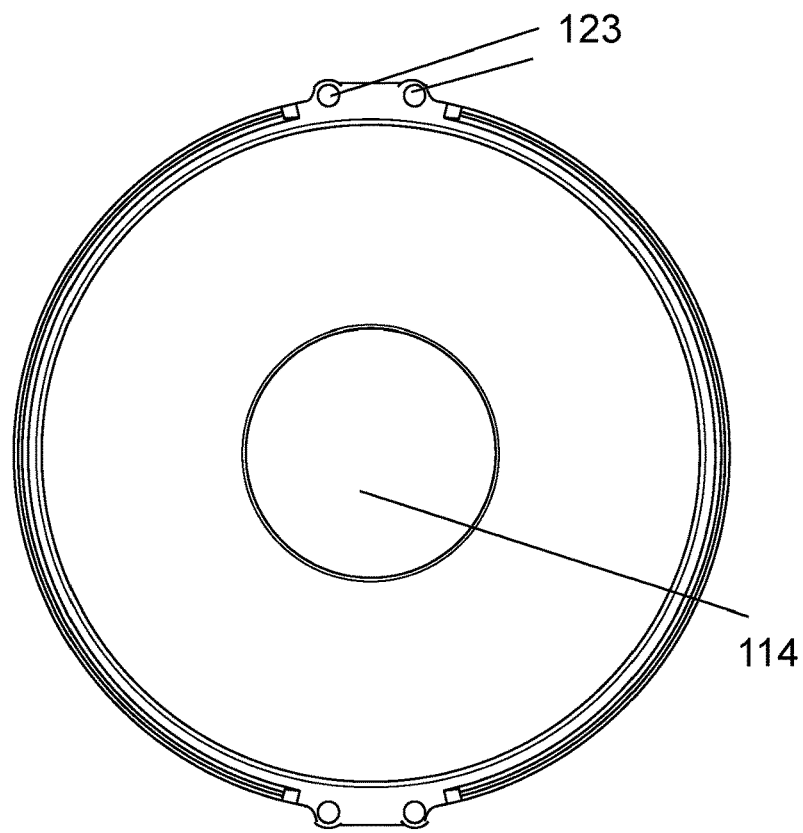
FIG. 3B is a top view of a funnel of the earplug dispenser of FIG. 1.

According to the embodiment as illustrated in FIGS. 3A and 3B, the funnel 108 includes a plurality of fingers 123 at a top opening 110. The fingers 123 are adapted to engage the complimentary receiver unit 143 (see also FIG. 4). The fingers 123 may also aid in securing the container 102 around the exterior surface 170 of the band 141 (see also FIG. 4).

Figure 4A:
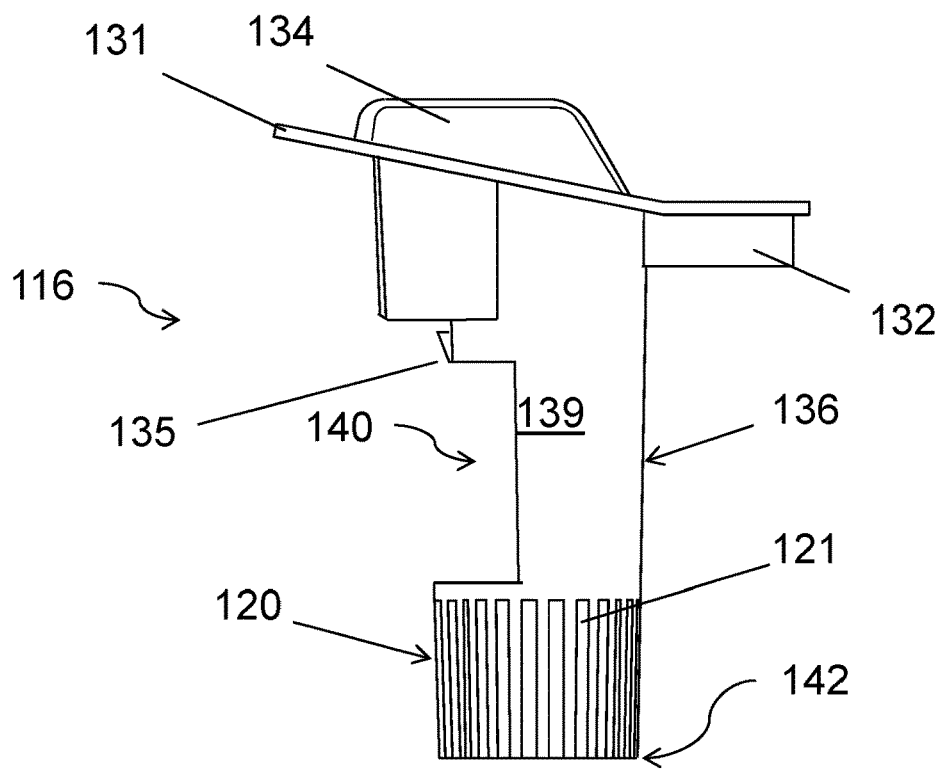
FIG. 4A is a side view of an impeller of the earplug dispenser of FIG. 1.
Figure 4B:
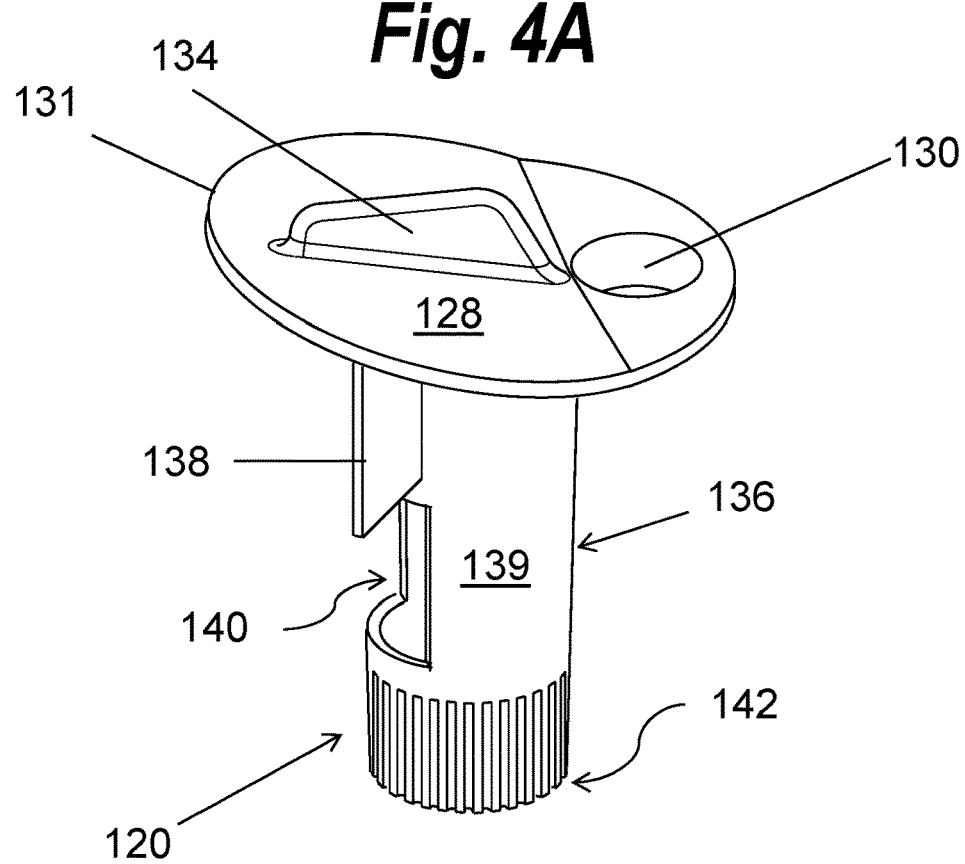
FIG. 4B is a top perspective view of an impeller of the earplug dispenser of FIG. 1.
Figure 4C:
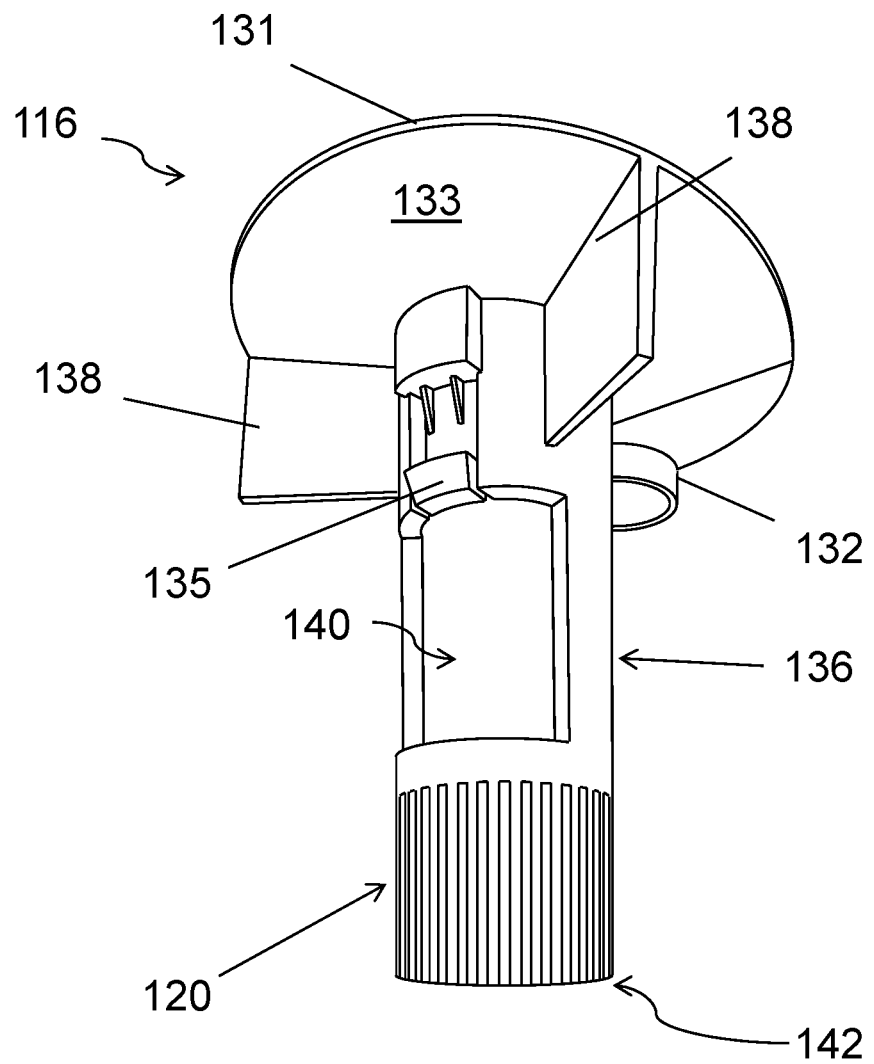
FIG. 4C is a side view of an impeller of the earplug dispenser of FIG. 1.

As illustrated in FIGS. 4A, 4B and 4C, the impeller 116 includes a top plate 131 having a top surface 128 and a bottom surface 133. The top surface 128 defines a single aperture 130 adapted to receive one or more earplugs 104. The aperture 130 incudes a lower collar 132 to direct one or more earplugs 104 falling through the aperture 130. As illustrated, the top surface 128 of the impeller 116 is angled for directing earplugs 104 to the impeller aperture 130. According to one embodiment, the angle is typically between about 5 degrees and about 85 degrees. At least one fin 134 extends upwards for agitating the earplugs 104 or breaking apart any sticking earplugs 104. A hollow shaft 136 extends downward from the bottom surface 133 of the top plate 131 and through the lower opening 114 of the funnel 108 when assembled (see e.g., FIGS. 1 and 7). As illustrated, two paddles 138 also extend from and along the bottom surface 133 of the top plate 131. The hollow shaft 136 includes a side surface 139 defining a recess 140. The recess 140 is in direct connection with a chute 142 at the bottom of the shaft 136. The shaft 136 further includes a knob portion 120 having a plurality of ribs 121 for improved grip upon rotation by a user in either a clockwise or counterclockwise direction. According to the embodiment shown in FIG. 4C, the impeller 116 further includes a flexible clip 135 that engages the central opening 148 of the barrier 118 (see also FIGS. 5 and 7) and secures the impeller 116 inside the central opening 148 yet allows the impeller 116 to be easily rotated by a user.

Figure 5:
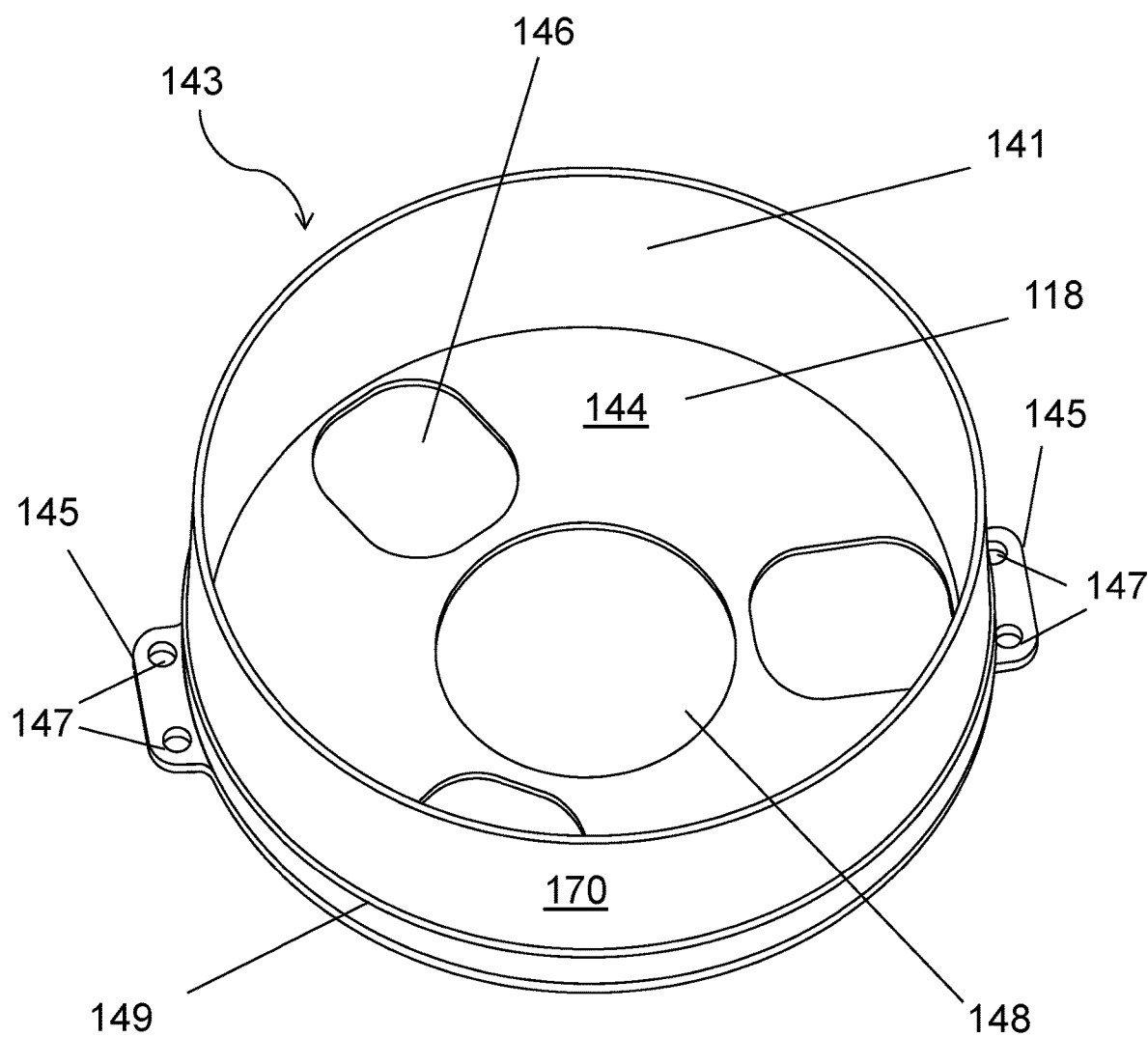
FIG. 5 is a top perspective view of a receiver unit of the earplug dispenser of FIG. 1.

FIG. 5 illustrates a receiver unit 143 according to one embodiment. The barrier 118 is secured to a band 141 to form the receiver unit 143. The receiver unit 143 includes a plurality of exterior braces 145 having a surface defining holes 147 adapted to engage and receive the fingers 123 of the funnel 108 (see FIGS. 3A and 3B). The barrier 118 includes an upper surface 144 defining a plurality of passages 146 that completely traverse the barrier 118. As illustrated, the barrier 118 includes three passages 146 that are independent. The three passages 146 are sized and adapted to regulate or otherwise control the delivery of earplugs 104 through the dispenser 100 (e.g., control the amount and position of plugs). The upper surface 144 of the barrier 118 further defines a central opening 148 that is annularly traversed by the impeller 116 (see e.g., FIGS. 1 and 7)).

According to one embodiment, the container 102 may be fabricated from any disposable or recyclable material. According to one embodiment, the container 102 is collapsible and foldable when not filled with earplugs 104. According to one embodiment, the container 102 is translucent or transparent thereby allowing a user to assess the need to replace an empty container 102. According to one embodiment, the container 102 is opaque, shaded or colored. The container 102 may be of any shape and size suitable for storing earplugs. According to one embodiment, the container 102 is a shape or size that is readily available for purchase from multiple suppliers thereby allowing quick and efficient filling with earplugs 104 and placement directly into use.

According to embodiment, the container 102 is fabricated from plastic. According to one embodiment, the container 102 is fabricated from corrugated plastic. According to a particular embodiment, the container 102 is a plastic bag. According to another embodiment, the container 102 is fabricated from paper. According to a particular embodiment, the container 102 is a paper bag. According to one embodiment, the container 102 is fabricated from a heavy-duty paper such as, for example, cardboard or fiberboard. According to one embodiment, the container 102 is fabricated from corrugated paper (e.g., corrugated cardboard or corrugated fiberboard). According to one embodiment, the container 102 is fabricated from corrugated heavy-duty paper or other paper-based material such as, for example, cardboard or fiberboard. According to such an embodiment, the physical characteristics of the corrugated heavy-duty paper or paper-based material may be adjusted to meet the storage and strength required of an earplug container. Such physical characteristics include, but are not limited to, flute size, combining adhesive, and linerboard design.

Figure 6B:
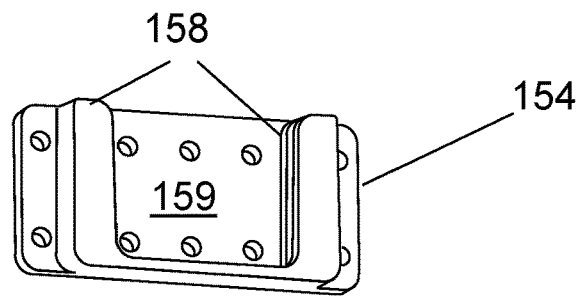
FIG. 6B is a side perspective view of a wall bracket component of a mounting system for an earplug dispenser according to one embodiment.
Figure 6A:
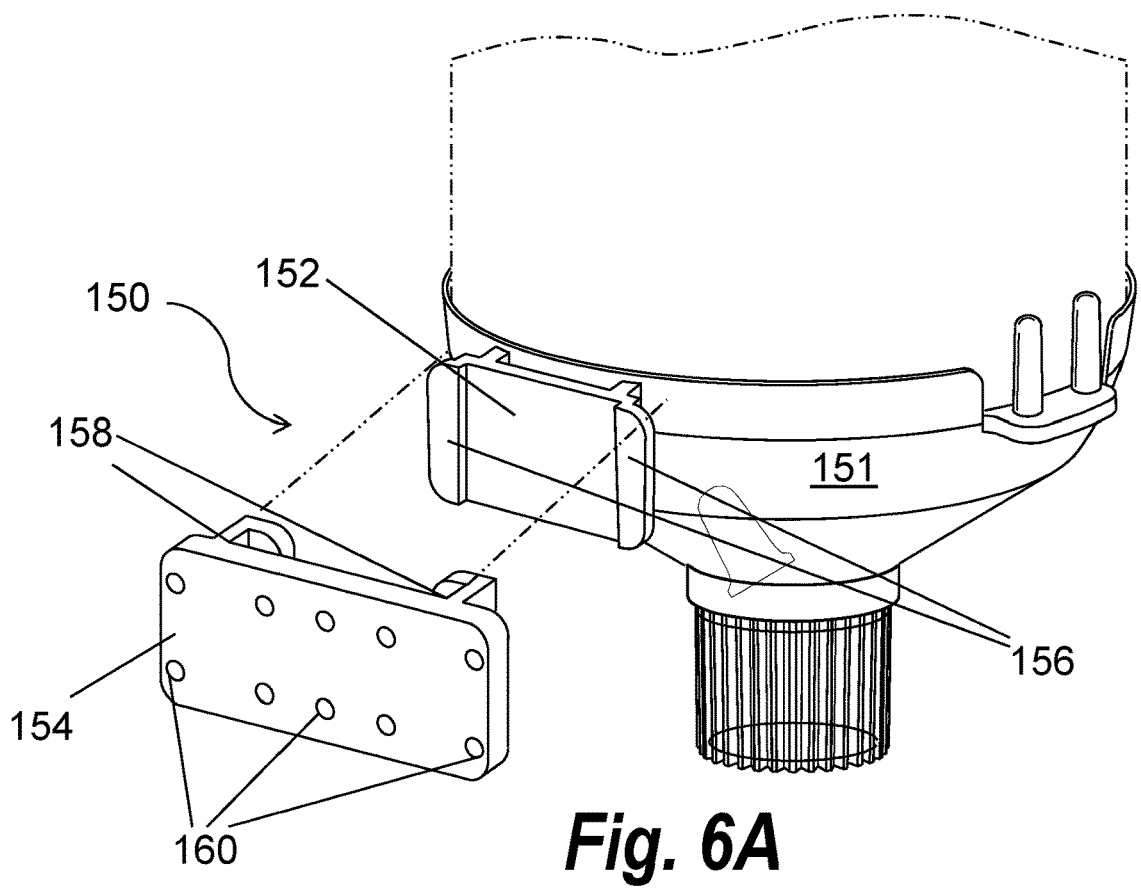
FIG. 6A is a perspective, blown apart view of a mounting system for an earplug dispenser according to one embodiment.
Figure 6C:
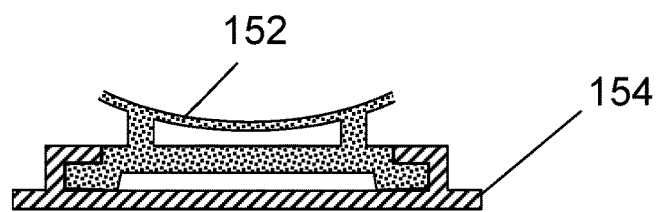
FIG. 6C is a top view of a mounting system for an earplug dispenser according to one embodiment.

A mounting system 150 for the earplug dispenser is illustrated in FIGS. 6A, 6B, and 6C. The mounting system 150 includes a mount 152 and a bracket 154. The mount 152 is secured directly to an exterior surface 151 of the funnel 108 or molded as a part of the funnel 108 during fabrication of the funnel 108. The mount 152 is adapted to engage a bracket 154. As illustrated, the mount 152 includes two flanges 156 that engage or slide within recesses 158 in the corresponding bracket 154. The bracket 154 includes a surface 159 defining a plurality of openings 160 for receiving an attachment means (not shown). Suitable attachment means include nails or screws. The bracket 154 may be attached to any vertical surface (e.g., a wall, bookshelf, etc.) and placed in convenient location for users (e.g., industrial workers) to quickly and efficiently obtaining earplugs 104 upon returning to work. The mount 152 and bracket 154 may be fabricated from any suitable material capable of supporting the weight of a filled dispenser 100. An exemplary suitable material is an injection molded plastic. The mount 152, bracket 154, or both may be opaque, shaded, colored, translucent, or transparent.

The funnel 108, impeller 116, and barrier 118 may be fabricated from any disposable or recyclable material such as, for example, plastic. According to one embodiment, the funnel 108, impeller 116, and barrier 118 are translucent or transparent thereby allowing a user to view the movement of one or more earplugs during delivery (see e.g., FIG. 1). According to an alternative embodiment, the impeller 116 and barrier 118 are fabricated from an opaque, shaded or colored material.

Figure 7:
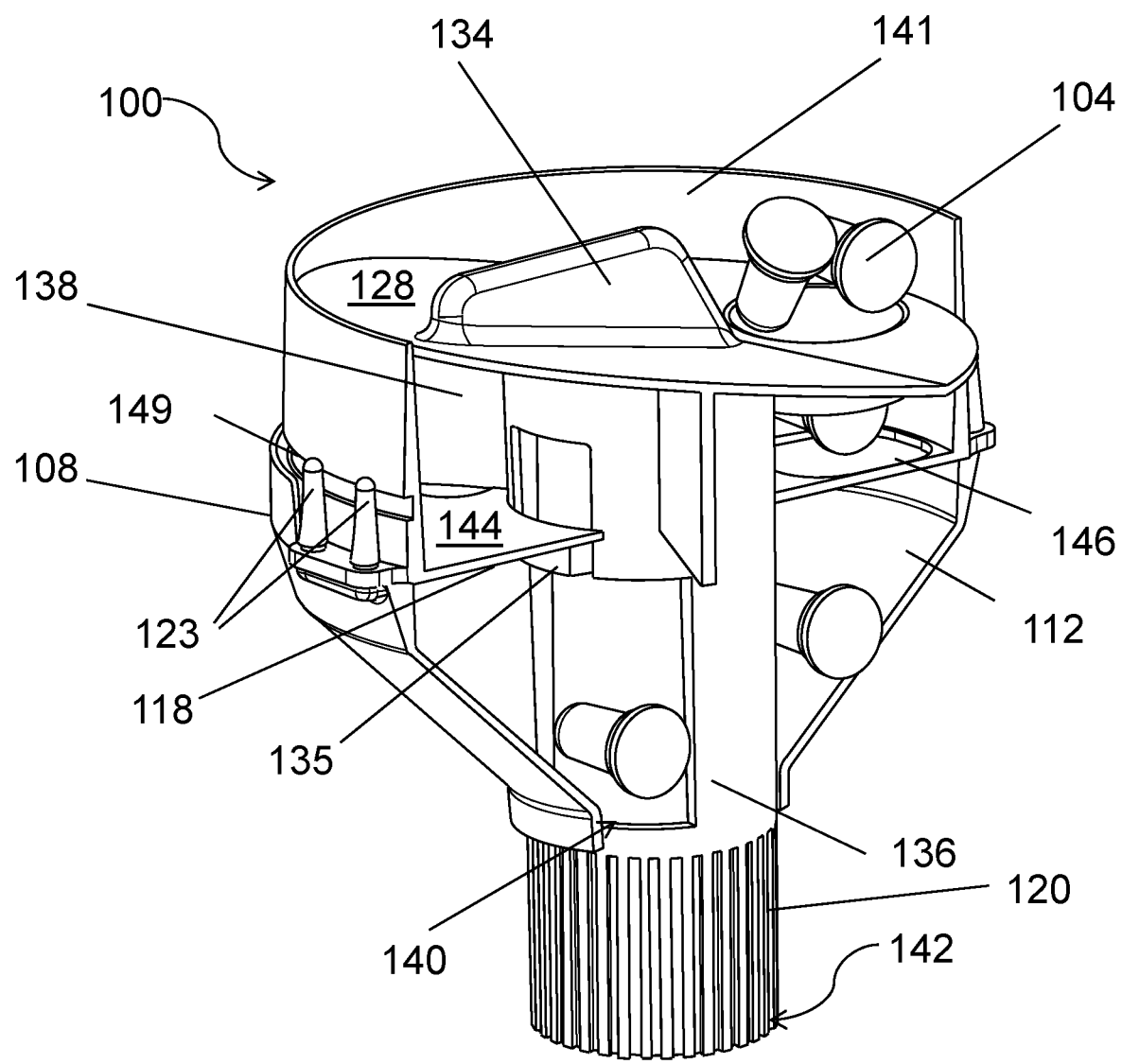
FIG. 7 is a cross-section view illustrating the path of earplugs through the earplug dispenser of FIG. 1.

The typical path of one or more earplugs 104 through two dispenser 100 embodiments during typical operation is illustrated in the FIG. 7. Upon turning the knob 120, the fin 134 agitates the earplugs 104 or breaks apart any sticking earplugs 104. Once agitated and loose, the one or more earplugs 104 fall down the angled top surface 128 toward the aperture 130. The earplugs 104 then fall through the aperture 130 and either directly onto the upper surface 144 of the barrier 118 or directly through a passage 146. The barrier 118 is located at a distance below the lower collar 132 such that earplugs 104 falling onto the barrier 118 are not pinched, jammed, squeezed or otherwise damaged upon turning the impeller 116. At least two paddles 138 sweep any earplugs 104 sitting on the upper surface 144 of the barrier 118 into one of the passages 146 and through to the tapered portion 112 of the funnel 108. Once the impeller 116 is rotated, the shaft recess 140 aligns with any earplugs 104 in the tapered portion 112 allowing the earplugs 104 to enter the recess 140 and fall through the hollow shaft 136 and out the chute 142 into the users hand or palm (see also FIG. 1). As illustrated, the aperture 130 is approximately 180 degrees opposite from the recess 140 which, according to one embodiment, allows earplugs 104 to sequentially align around the hollow shaft 136 in the tapered portion 112 of the funnel 108. Alignment around the shaft 136 allows the earplugs 104 to be fed into the recess 140 in single file fashion thereby reducing delivery of more than the desired number of earplugs 104.

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

We claim:

1. A dispenser for delivering earplugs to a user comprising
   a cardboard or fiberboard container for storing earplugs until delivered to the user, the container including a transparent or translucent window and a mouth;
   a funnel having a top opening and a lower opening;
   a receiver unit including a band and a barrier, the barrier having a surface defining a plurality of passages and a central opening; and
   a rotatable impeller comprising a flexible clip to engage a central opening of the barrier,
   wherein the mouth of the container engages the band of the receiver unit,
   wherein a mount is secured to an exterior surface of the funnel, and
   wherein the funnel includes a plurality of fingers adapted to engage a surface defining holes within braces located on the receiver unit.

2. The dispenser of claim 1, wherein the rotatable impeller further comprises (i) a top plate having a top surface defining a single aperture adapted to receive one or more earplugs; (ii) a plurality of paddles extending from a bottom surface of the top plate; and (iii) a hollow shaft extending downward from the bottom surface of the top plate and adapted to engage the central opening of the barrier.

3. The dispenser of claim 1, wherein the impeller is adapted to move in both a clockwise and counterclockwise manner.

4. The dispenser of claim 1, wherein the mount includes at least two flanges adapted to engage a bracket.

5. The dispenser of claim 4, wherein the bracket, mount, or both the bracket and mount are manufactured from an opaque, shaded, colored, translucent, or transparent material.

6. The dispenser of claim 4, wherein the bracket includes a surface defining a plurality of openings adapted to receive an attachment means nail or screw.

7. The dispenser of claim 2, wherein the hollow shaft further comprises: (i) a side surface defining a shaft recess for receiving one or more earplugs; and (ii) a chute in direct communication with the shaft recess for delivering one or more earplugs entering the recess to a user.

8. The dispenser of claim 7, wherein the shaft recess is 180 degrees opposite the impeller aperture.

9. The dispenser of claim 1, wherein one or more of the container, impeller, barrier, or funnel are fabricated from an opaque, shaded, colored, translucent, or transparent material.

10. The dispenser of claim 2, wherein a substantial portion of the top surface of the top plate is angled for directing earplugs to the impeller aperture.

11. The dispenser of claim 10, wherein the top surface angle is between 5 and 85 degrees.

12. The dispenser of claim 2, wherein the top surface of the top plate includes a fin extending upward for agitating earplugs to facilitate movement toward the impeller aperture.

13. The dispenser of claim 2, wherein the hollow shaft includes a knob portion, the knob portion including a plurality of ribs for gripping and rotating by the user.

14. The dispenser of claim 1, wherein the impeller includes two paddles for sweeping at least one earplug into a barrier passage.

\* \* \* \* \*